United States Patent
Tanzawa et al.

(10) Patent No.: US 7,531,462 B2
(45) Date of Patent: May 12, 2009

(54) METHOD OF INSPECTING SEMICONDUCTOR WAFER

(75) Inventors: Katsujiro Tanzawa, Yokohama (JP); Norihiko Tsuchiya, Tokyo (JP); Junji Sugamoto, Yokosuka (JP); Yukihiro Ushiku, Yokohama (JP)

(73) Assignee: Kabushiki Kaisha Toshiba, Tokyo (JP)

( * ) Notice: Subject to any disclaimer, the term of this patent is extended or adjusted under 35 U.S.C. 154(b) by 277 days.

(21) Appl. No.: 11/444,301

(22) Filed: Jun. 1, 2006

(65) Prior Publication Data
US 2006/0281281 A1 Dec. 14, 2006

(30) Foreign Application Priority Data
Jun. 13, 2005 (JP) ............... 2005-172642

(51) Int. Cl.
*H01L 21/302* (2006.01)
(52) U.S. Cl. .................................. 438/745
(58) Field of Classification Search ............ 438/4, 438/30, 239, 22, 197–200, 14–17, 149, 795, 438/79, 766, 758, 745, 689, 680, 513, 458–489, 438/455, 45, 431
See application file for complete search history.

(56) References Cited

U.S. PATENT DOCUMENTS 5,271,796 A 12/1993 Miyashita et al.
2002/0022348 A1* 2/2002 Sakaguchi et al. .......... 438/480
2002/0098421 A1* 7/2002 Hasegawa et al. ............ 430/5
2004/0137752 A1* 7/2004 Sugamoto et al. .......... 438/745
2005/0023656 A1* 2/2005 Leedy ........................ 257/678
2007/0117239 A1* 5/2007 Ishi .............................. 438/30

FOREIGN PATENT DOCUMENTS

JP 2004-179638 6/2004

* cited by examiner

Primary Examiner—Charles D. Garber
Assistant Examiner—Andre' C Stevenson
(74) Attorney, Agent, or Firm—Finnegan, Henderson, Farabow, Garrett & Dunner, L.L.P.

(57) ABSTRACT

A method of inspecting a semiconductor wafer, comprises removing a device structure film on the semiconductor wafer with a chemical solution to expose a crystal surface of the semiconductor wafer; coating a protected area, which is a part of the crystal surface of the semiconductor wafer, with a mask material for protecting the crystal surface of the semiconductor wafer; etching the semiconductor wafer selectively, thereby making a crystal defect in a non-protected area, which is a part of the crystal surface of the semiconductor wafer that is not coated with the mask material, appear after the crystal surface is coated with the mask material; removing the mask material after the selective etching; carrying out quantitative measurement of the protected area and the non-protected area using an optical defect inspection apparatus or a beam-type defect inspection apparatus; and calculating the number of crystal defects of the semiconductor wafer base on the result of the measurement.

14 Claims, 7 Drawing Sheets

| CHIP SYMBOL | PROTECTED AREA | TREATMENT | MEANS FOR DEFECT MEASUREMENT | MEASUREMENT VALUE OBTANIED BY OPTICAL DEFECT INSPECTION APPARATUS (DEFECTS/cm²) | CRYSTAL DEFECT DENSITY (DEFECTS/cm²) |
|---|---|---|---|---|---|
| a | THIRD | NO COMPLETE REMOVAL, NO SELECTIVE ETCHING | TEM | ----- | 6100 |
| b | FOURTH | COMPLETE REMOVAL, NO SELECTIVE ETCHING | DEFECT INSPECTION APPARATUS | 21500 | ----- |
| c | FOURTH | COMPLETE REMOVAL, NO SELECTIVE ETCHING | DEFECT INSPECTION APPARATUS | 20500 | ----- |
| d | NON-PROTECTED | COMPLETE REMOVAL, SELECTIVE ETCHING | DEFECT INSPECTION APPARATUS | 26500 | 5500 |
| | | | SEM | ----- | 5900 |
| e | NON-PROTECTED | COMPLETE REMOVAL, SELECTIVE ETCHING | DEFECT INSPECTION APPARATUS | 26900 | 5400 |
| f | NON-PROTECTED | COMPLETE REMOVAL, SELECTIVE ETCHING | DEFECT INSPECTION APPARATUS | 26700 | 6200 |

FIG. 10

METHOD OF INSPECTING SEMICONDUCTOR WAFER

CROSS-REFERENCE TO RELATED APPLICATION

This application is based upon and claims the benefit of priority from the prior Japanese Patent Application No. 2005-172642, filed on Jun. 13, 2005, the entire contents of which are incorporated herein by reference.

BACKGROUND OF THE INVENTION

1. Field of the Invention

The present invention relates to a method of processing and a method of inspecting a semiconductor wafer having a device pattern formed thereon. In particular, it relates to a method of inspecting a semiconductor wafer for a crystal defect using an optical or electron-beam-type defect inspection apparatus.

2. Background Art

Conventionally, in manufacturing semiconductor devices, a thermal stress or membrane stress occurring during the device manufacture process causes degradation of characteristics of the semiconductor device to cause a dislocation, which causes a disadvantageous leakage, insufficient withstand voltage or the like.

According to a conventional method of detecting such a dislocation, a structure film (stack film) over the whole surface of the wafer on which a semiconductor device is formed is completely removed before the wafer is selectively etched to make any crystal defect appear, and then, the crystal defect is detected using image recognition by an optical or electron-beam-type defect inspection apparatus.

In the inspection method described above, a pit or residue other than a crystal defect (dislocation) that is generated due to the complete removal or the selective etching occurs. When the defect inspection apparatus described above is used to measure crystal defects, such a pit or residue is perceived as a crystal defect because it cannot be discriminated from crystal defects and, therefore, the pit or residue becomes noise.

According to a conventional method of reducing such a noise component, after the device structure film is removed, the semiconductor wafer is quantitatively measured by image recognition by an optical defect inspection apparatus, and after the selective etching, the semiconductor wafer is quantitatively measured again. Then, the difference between the two measurement results is calculated to cancel the noise component, and the difference is regarded as the number of crystal defects that are made to appear by the selective etching (see Japanese Patent Laid-Open No. 2004-179638, for example).

However, in the conventional method described above, for example, before the second quantitative measurement after the selective etching of the semiconductor wafer, an SPM treatment is carried out to remove Cr that has been contained in a Wright solution used for the selective etching, and then, cleaning using a diluted HF solution, rinsing with water, and drying using a spin drier are sequentially carried out. In the case where particles or residues that have existed on the semiconductor wafer before the first quantitative measurement are removed by the treatments after the selective etching, the particles or residues (noise components) that should be cancelled by the difference between the two quantitative measurement results are not detected by the second quantitative measurement.

That is, there is a problem that the calculated difference between the measured values obtained by the quantitative measurements still contains the noise components of particles or residues falsely perceived as crystal defects and is different from the number of crystal defects that are made to appear by the selective etching.

SUMMARY OF THE INVENTION

According one aspect of the present invention, there is provided: a method of inspecting a semiconductor wafer, comprising removing a device structure film on the semiconductor wafer with a chemical solution to expose a crystal surface of the semiconductor wafer; coating a protected area, which is a part of the crystal surface of the semiconductor wafer, with a mask material for protecting the crystal surface of the semiconductor wafer; etching selectively the semiconductor wafer, thereby making a crystal defect in a non-protected area, which is a part of the crystal surface of the semiconductor wafer that is not coated with the mask material, appear after the crystal surface is coated with the mask material; removing the mask material after the selective etching; carrying out quantitative measurement of the protected area and the non-protected area using an optical defect inspection apparatus or a beam-type defect inspection apparatus; and calculating the number of crystal defects of the semiconductor wafer base on the result of the measurement.

BRIEF DESCRIPTION OF THE DRAWINGS

FIG. 10 shows measurement results obtained by the method of inspecting a semiconductor wafer according to the third embodiment of the present invention.

DETAILED DESCRIPTION

Embodiments of the present invention will now be described in more detail with reference to the drawings. In the following description of the embodiments, "dislocation", which is a kind of line defects in the atomic arrangement, will be particularly described as a representative crystal defect of a semiconductor crystal constituting a substrate. However, other crystal defects (such as an oxidation-induced stacking fault (OSF) and a void defect) can also be evaluated, and evaluations described in this specification include evaluations of such other crystal defects. The "dislocation" can be made to appear in the form of an etch pit having a longer diameter of about 0.1 μm to about 10 μm by selective etching.

First Embodiment

According to a first embodiment, a non-protected area of a semiconductor wafer that has been subjected to treatments including selective etching and a protected area of the same semiconductor that has been subjected to the same treatments excluding selective etching are quantitatively measured by a defect inspection apparatus capable of quantitatively evaluating any crystal defect by image recognition. Then, based on the assumption that the measured value for the non-protected area includes the number of crystal defects that are made to appear by the selective etching and the number of pits or residues that are generated due to the complete removal of the semiconductor device structure and perceived as crystal defects, the difference between the measured value for the non-protected area and the measured value for the protected area is calculated to cancel the noise component of the pit or residues generated due to the complete removal of the semiconductor device structure.

In this way, the number of crystal defects of the semiconductor wafer that are generated because of the manufacture process condition or the like is determined more accurately.

Figure 1:
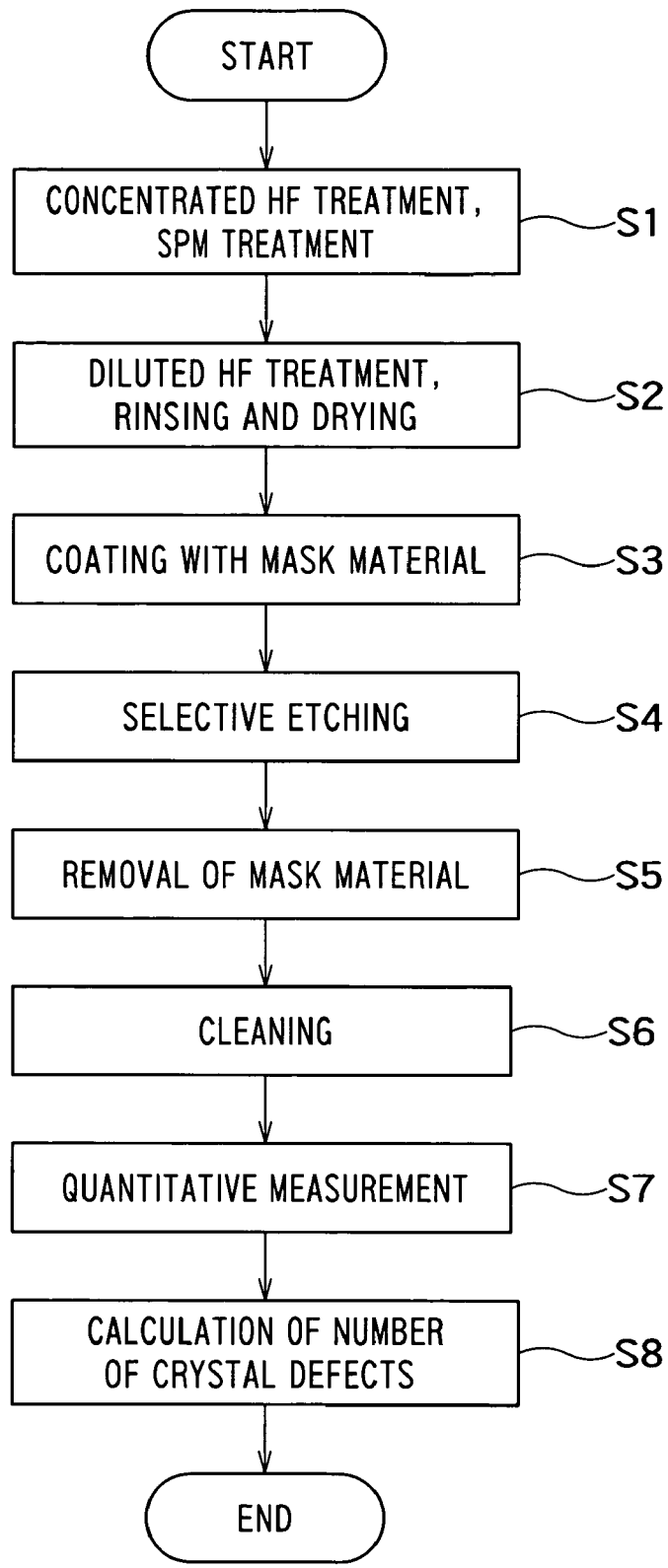
FIG. 1 is a flowchart showing a method of inspecting a semiconductor wafer according to a first embodiment of the present invention.

Now, a method of inspecting a semiconductor wafer according to the first embodiment of the present invention will be described with reference to the drawings. FIG. 1 is a flowchart showing the method of inspecting a semiconductor wafer according to the first embodiment of the present invention.

First, a device structure film on a semiconductor wafer to be evaluated is removed by a chemical solution to expose the crystal surface of the semiconductor wafer (step S1). The semiconductor wafer is immersed in a concentrated HF solution (49% $HF:H_2O=1:2$ (further containing 1% of surface active agent NCW)) for 15 minutes and then rinsed with water. Then, the semiconductor wafer is treated with a sulfuric-hydrogen peroxide mixture (SPM) solution ($H_2SO_4$: $H_2O_2=5:2$) for 10 minutes and then rinsed with water.

After step S1, the semiconductor wafer is treated with a diluted HF solution (40% HF) for 30 minutes to remove any remaining film (a residue of a gate electrode, for example), rinsed with water, and then dried with a spin drier (step S2).

Through steps S1 and S2 described above, the structure film of the semiconductor device is completely removed.

Then, a protected area, which is a part of the crystal surface of the semiconductor wafer, is coated with a mask material that protects the crystal surface of the semiconductor wafer (step S3). For example, the mask material may be a tetrafluoroethylene tape, polyimide tape, a resist or a wax.

In the case where the mask material has to be resistant to etching, the tetrafluoroethylene tape can preferably be used. Furthermore, in this embodiment, selective etching is carried out for a short duration, specifically, 5 seconds. In this case, a resist that is suitable for patterning can be used as the mask material.

Figure 2:
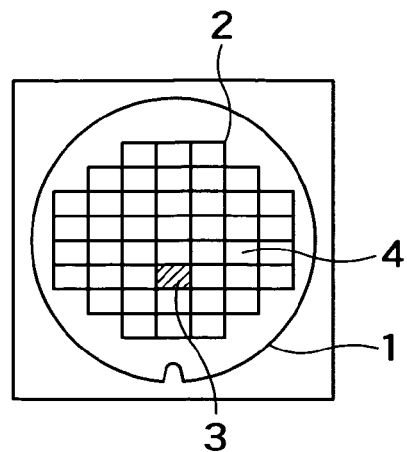
FIG. 2 is a plan view of a semiconductor wafer coated with a mask material according to the method of inspecting a semiconductor wafer according to the first embodiment of the present invention.
Figure 3:
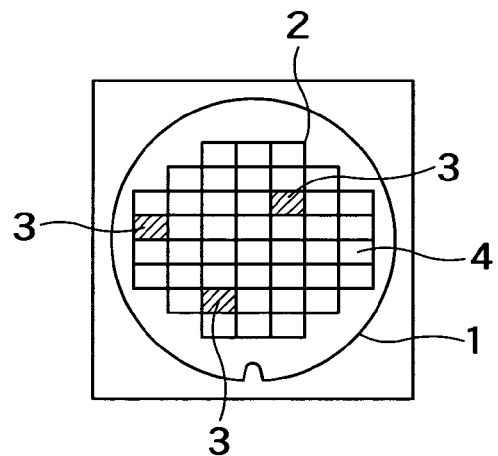
FIG. 3 is a plan view of a semiconductor wafer coated with a mask material according to the method of inspecting a semiconductor wafer according to the first embodiment of the present invention.
Figure 4:
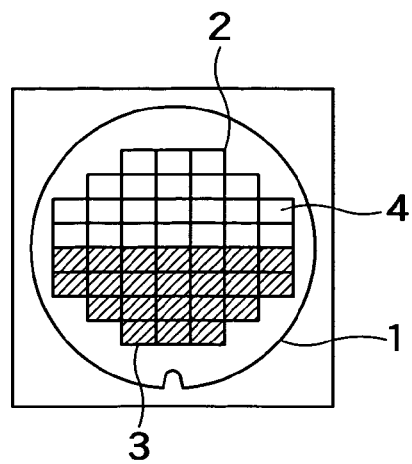
FIG. 4 is a plan view of a semiconductor wafer coated with a mask material according to the method of inspecting a semiconductor wafer according to the first embodiment of the present invention.

FIGS. 2 to 4 are plan views of exemplary semiconductor wafers coated with a mask material in the method of inspecting a semiconductor wafer according to the first embodiment of the present invention. As shown in FIGS. 2 to 4, taking variations in the surface of each wafer into account, a plurality of protected areas 3 may be provided for a plurality of areas 2, each of which is to constitute one chip, in the crystal surface of each semiconductor wafer 1, and each of the protected areas 3 may be coated with a mask material. In this way, the surface of one semiconductor wafer 1 is divided into the protected area 3 and a non-protected area 4.

Then, after the crystal surface is coated with the mask material in step S3, each semiconductor wafer is selectively etched to make a crystal defect in the non-protected area, which is the crystal surface of the semiconductor wafer that is not coated with the mask material, appear (step S4).

The selective etching involves immersing each semiconductor wafer in a Wright solution (containing HF (60 ml), $HNO_3$ (30 ml), $Cu(NO_3)$ (2 g), 5-mol $CrO_3$ (30 ml), $CH_3COOH$ (60 ml), and $H_2O$ (60 ml), for example) for one to five seconds. After that, each semiconductor wafer is immersed in water for 30 seconds to stop the selective etching.

Then, after step S4, each semiconductor wafer is rinsed with water as a preparation for removing the mask material, that is, the tetrafluoroethylene tape, the polyimide tape or the resist, from each semiconductor wafer (step S5). These mask materials can be removed by an organic solvent, such as thinner. Furthermore, the tetrafluoroethylene tape and the polyimide tape can be peeled-off with tweezers or the like. The resist may be removed by ashing or an SPM processing.

After the mask material is removed in step S5, each semiconductor wafer is cleaned (step S6). For example, this cleaning involves treating the semiconductor wafer with an SPM solution ($H_2SO_4:H_2O_2=2:5$) for 10 minutes to remove a small amount of chromium remaining on the semiconductor wafer, treating the semiconductor wafer with an APM solution ($NH_4OH/H_2O_2/H_2O$) or hydrogen chloride-hydrogen peroxide mixture (HPM) solution ($HCl/(H_2O_2)/H_2O$) containing ozone water for 10 minutes, and then rinsing the semiconductor wafer with water. After the cleaning, each semiconductor wafer is dried with a spin drier.

By the process described above, a pretreatment for inspection of a semiconductor wafer for a crystal defect is completed.

Then, the protected area and the non-protected area of each semiconductor wafer are quantitatively measured by an optical defect inspection apparatus or beam-type defect inspection apparatus capable of evaluating each wafer by image recognition (step S7). For example, the evaluation by the defect inspection apparatus based on image recognition is to detect a crystal defect by comparing the area (pattern) to be evaluated with a reference area (pattern) to recognize the difference therebetween or the like.

Then, based on the measurement result, the number of crystal defects of the semiconductor wafer is calculated (step S8). That is, based on the different between the measured value for the protected area and the measured value for the non-protected area, any noise (any etch pit or structure film residue that is not a crystal defect) is removed from the measured values to calculate the number of crystal defects of the semiconductor wafer.

Here, if measurement is carried out for a protected area and a non-protected area adjacent to the protected area, and the difference between the measured value for the protected area and the measured value for the non-protected area is calculated, the effect of the in-plane variations of the calculated number of crystal defects of the semiconductor wafer can be reduced.

Through the steps described above, the method of inspecting a semiconductor wafer according to this embodiment is completed.

Here, crystal defects of semiconductor wafers having a semiconductor device structure film formed thereon were measured according to the flow shown in FIG. 1. Furthermore, chips were cut from the wafers, and crystal defects of the chips were detected and directly measured by a scanning electron microscope (SEM). Now, the result of comparison between the measured values will be described.

First, three 8-inch semiconductor wafers "A", "B" and "C" each having semiconductor device structure film formed thereon as described below were prepared as evaluation samples and treated according to the method of inspecting a semiconductor wafer according to this embodiment to quantitatively measure the crystal defects thereof.

In the wafer "A", one chip was designated as a protected area as shown in FIG. 2, and a tetrafluoroethylene tape as a mask material was applied to the protected area to cover the chip. In the wafer "B", three chips were designated as protected areas as shown in FIG. 3, and polyimide tapes as a mask material were applied to the protected areas to cover the chips. In addition, in the wafer "C", twenty-two chips, which are a half of the chips in the wafer, were designated as protected areas as shown in FIG. 4, and the protected areas were coated with a semiconductor resist as a mask material for protection.

Quantitative measurement of crystal defects in the semiconductor device area of the semiconductor wafers "A" and "B" was carried out with an optical defect inspection apparatus. Quantitative measurement of crystal defects in the semiconductor device area of the semiconductor wafer "C" was carried out with an electron-beam-type defect inspection apparatus. However, the quantitative measurement of crystal defects based on image recognition can be carried out with the optical defect inspection apparatus or the electron-beam-type defect inspection apparatus.

The results of quantitative measurement of the semiconductor wafer "A" under the conditions described above were as follows. That is, the quantitative measured value (a) for the non-protected area was 28500 defects/cm$^2$, and the quantitative measured value (b) for the protected area was 26200 defects/cm$^2$. Therefore, the number of crystal defects (a-b) of the wafer A, which is determined by the difference between the quantitative measured value (a) for the non-protected area and the quantitative measured value (b) for the protected area, was 2300 defects/cm$^2$.

Similarly, as for the semiconductor wafer "B", the quantitative measured value (a) for the non-protected area was 64700 defects/cm$^2$, and the quantitative measured value (b) for the protected area was 59500 defects/cm$^2$. Therefore, the number of crystal defects (a-b) of the wafer "B" was 5200 defects/cm$^2$.

Similarly, as for the semiconductor wafer "C", the quantitative measured value (a) for the non-protected area was 88300 defects/cm$^2$, and the quantitative measured value (b) for the protected area was 87200 defects/cm$^2$. Therefore, the number of crystal defects (a-b) of the wafer "C" was 1100 defects/cm$^2$.

Here, since the protected area is not subjected to the selective etching as described above, the quantitative measured value (b) for the protected area is considered to include pits or residues of the semiconductor device structure film that are generated due to the complete removal of the semiconductor device structure film and detected as crystal defects by the optical or electron-beam-type defect inspection apparatus.

Then, the reliability of the crystal defect densities of the semiconductor wafers "A", "B" and "C" determined by the method of inspecting a semiconductor wafer according to this embodiment was verified by comparison with the measurement result obtained by the SEM. As comparison samples, a chip of the protected area protected with the mask material was cut from each of the semiconductor wafers "A", "B" and "C", the chips were selectively etched under the same conditions as described above, and only dislocations, which are an intended crystal defect, were measured by the SEM. The results of measurement for these samples were as follows. That is, the number of crystal defects of the semiconductor wafer "A" was 2200 defects/cm$^2$, the number of crystal defects of the semiconductor wafer "B" was 4750 defects/cm$^2$, and the number of crystal defects of the semiconductor wafer "C" was 1550 defects/cm$^2$.

As can be seen form the above description, the crystal defect densities determined by the method according to the present invention substantially coincide with the dislocation densities of the chips cut from the respective wafers determined by SEM photographic observation. Thus, it is proven that the method of inspecting a semiconductor wafer according to this embodiment can provide a value from which the effect of noise is sufficiently reduced.

As described above, according to the method of inspecting a semiconductor wafer according to this embodiment, the effect of noise, such as a pit or residue generated due to the complete removal of the semiconductor device structure film, on the measured value is reduced, and thus, the number of crystal defects of the semiconductor wafer can be more accurately measured and evaluated. Accordingly, for example, the relationship between the electrical property of the semiconductor device and the crystal defect can be clarified, and furthermore, the semiconductor device manufacturing process can be improved, and the production yield can be improved.

In addition, since the crystal defects can be quantitatively evaluated over the entire surface of the semiconductor wafer on which the semiconductor device is formed by image recognition by the defect inspection apparatus, the inspection time can be reduced.

Second Embodiment

With regard to the first embodiment, there has been described an inspection method of measuring crystal defects generated because of a manufacture process condition or the like by excluding noise factors, such as a pit or residue generated due to the complete removal of the semiconductor device structure film. However, with regard to a second embodiment, an inspection method for measuring noise, such as a pit or residue generated due to the complete removal of the semiconductor device structure, will be described in particular.

Figure 5:
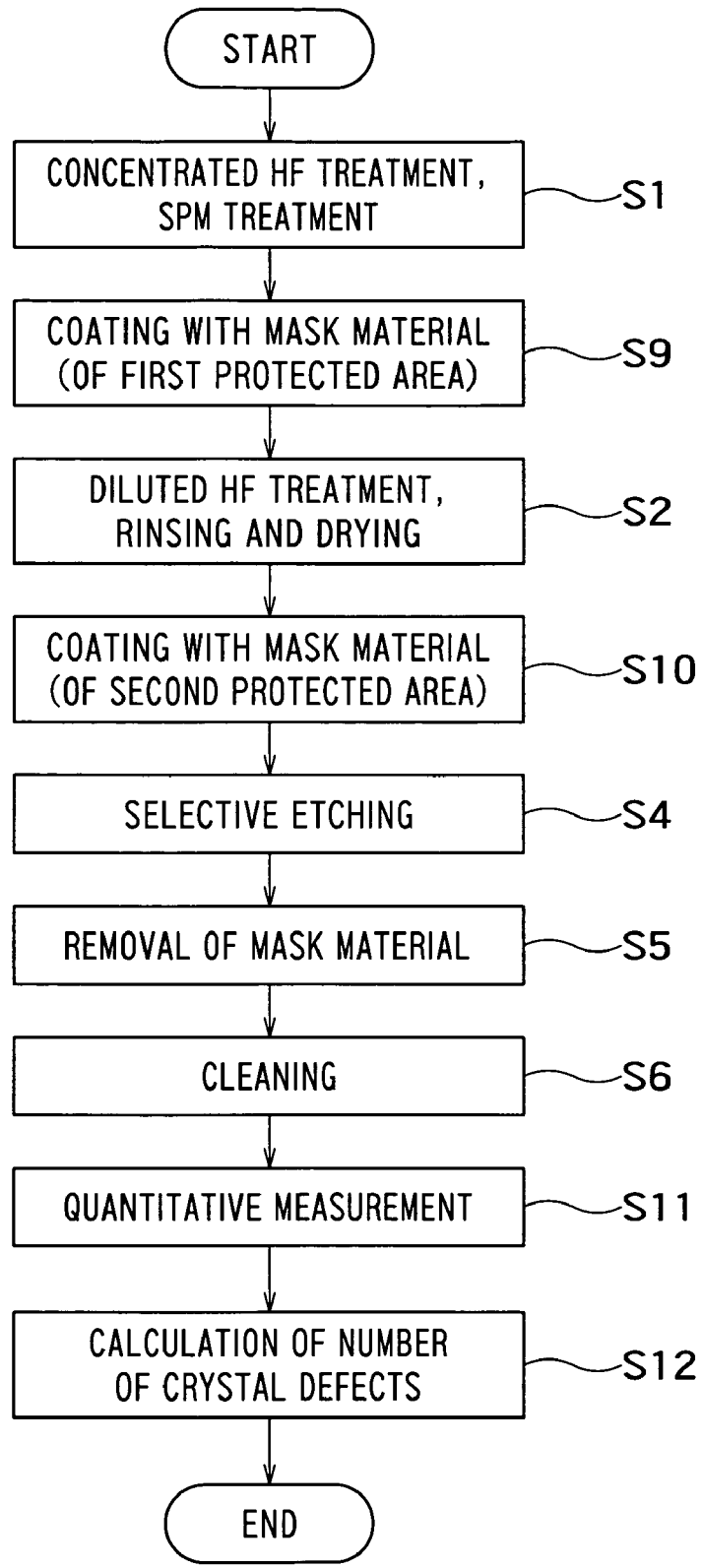
FIG. 5 is a flowchart showing a method of inspecting a semiconductor wafer according to a second embodiment of the present invention.

In the following, a method of inspecting a semiconductor wafer according to the second embodiment will be described with reference to the drawings. FIG. 5 is a flowchart showing the method of inspecting a semiconductor wafer according to the second embodiment of the present invention.

As shown in FIG. 5, in the method of inspecting a semiconductor wafer according to this embodiment, after the semiconductor wafer is treated with a concentrated HF treatment and an SPM treatment as in the first embodiment (step S1), a first protected area, which is a part of the surface of the semiconductor wafer, is coated with a mask material (step S9). For example, taking into account the following diluted HF treatment or the like, a tetrafluoroethylene tape, which is relatively resistant to etching, is selected as the mask material.

After step S9, a diluted HF treatment and a rinsing and drying treatment are carried out as in the first embodiment (step S2) to completely remove the device structure film on the semiconductor wafer, thereby exposing the crystal surface of the semiconductor wafer.

Figure 6:
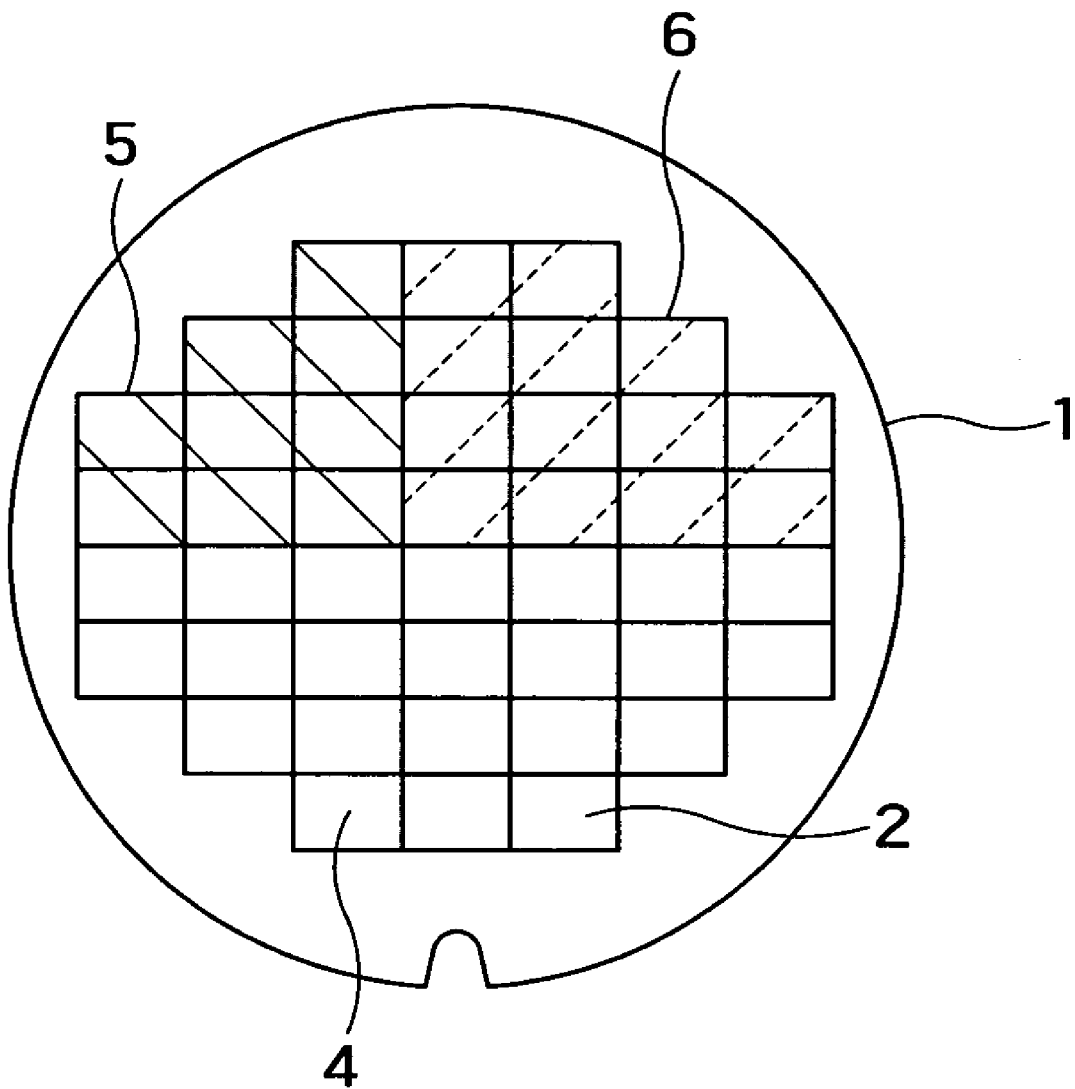
FIG. 6 is a plan view of a semiconductor wafer coated with a mask material according to the method of inspecting a semiconductor wafer according to the second embodiment of the present invention.

Then, a second protected area, which is a part of the surface of the semiconductor wafer other than the first protected area, is coated with a mask material (Step S10). Here, FIG. 6 shows an exemplary semiconductor wafer coated with a mask material in the method of inspecting a semiconductor wafer according to the second embodiment of the present invention. As shown in FIG. 6, the surface of the semiconductor wafer 1 is divided into a first protected area 5, a second protected area 6 and a non-protected area 4.

Then, the semiconductor wafer is selectively etched (step S4), the mask material is removed (step S5), and cleaning is performed (step S6). After that, the first protected area, the second protected area and the non-protected area, which is not protected by any mask material, are quantitatively measured by an optical defect inspection apparatus or a beam-type defect inspection apparatus (step S11).

Then, based on the measurement result, the number of crystal defects of the semiconductor wafer is calculated (step S12). As in the first embodiment, the number of relevant crystal defects of the semiconductor wafer that are generated because of a manufacture process or the like can be determined by calculating the difference between the quantitative measured value for the second protected area and the quantitative measured value for the non-protected area.

As described above, the first protected area is not subjected to the diluted HF treatment and the rinsing and drying treatment (step S2). Thus, the quantitative measured value for the first protected area is supposed to include, as noise, not only pits generated due to the concentrated HF treatment and the SPM treatment (step S1) but also residues of the device structure film (for example, residues of a gate electrode).

On the other hand, the second protected area is subjected to the diluted HF treatment and the rinsing and drying treatment (step S2). Thus, the quantitative measured value for the second protected area is supposed to include only pits generated due to the concentrated HF treatment and the SPM treatment (step S1) as noise.

Therefore, it is considered that the measured values of the residues of the device structure film that serve as noise can be extracted by calculating the difference between the measured values. Furthermore, it is considered that the conditions of the relevant diluted HF treatment and rinsing and drying treatment (step S2) can be controlled based on the value calculated.

In this way, in the case where the device structure film on the semiconductor wafer is removed in a plurality of steps (steps S1 and S2 in this embodiment), the first protected area, which is a part of the surface of the semiconductor wafer, is coated with a mask material during an interval between the steps. Then, the noise component in the quantitative measured value that is due to the processing after the coating with the mask material and before the selective etching is extracted. Based on the extracted value, the condition of the diluted HF treatment and the rinsing and drying treatment, that is, the condition of the complete removal of the semiconductor device structure can be improved (controlled).

As described above, according to the method of inspecting a semiconductor wafer according to this embodiment, the number of crystal defects generated because of a relevant manufacture process can be determined as in the first embodiment. In addition, since an area of the surface of the semiconductor wafer is coated with a mask material during an interval between processes of removing the device structure film on the semiconductor wafer, and the quantitative measurement is performed on the area, the noise component in the quantitative measured value that is generated due to the processing before the selective etching can be extracted. Thus, based on the extracted information, the condition of the complete removal of the semiconductor device structure film can be improved (controlled).

Third Embodiment

With regard to the first embodiment, there has been described an inspection method of measuring crystal defects generated because of a manufacture process condition or the like by excluding noise factors, such as a pit or residue generated due to the complete removal of the semiconductor device structure. However, with regard to an third embodiment, an inspection method that uses one wafer and measures crystal defects by photography observation by an SEM, a transmission electron microscope (TEM) or the like will be described in particular.

Figure 7:
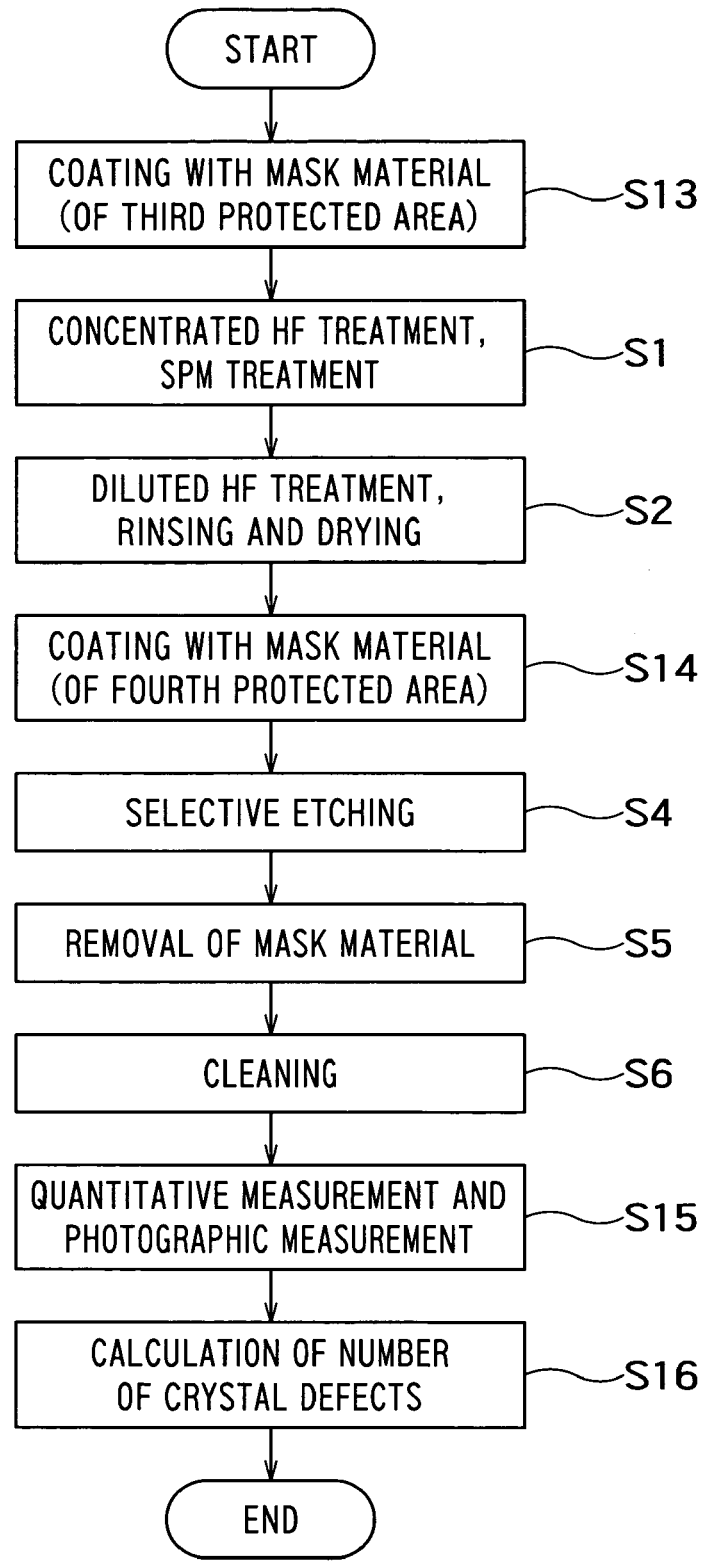
FIG. 7 is a flowchart showing a method of inspecting a semiconductor wafer according to a third embodiment of the present invention.

In the following, a method of inspecting a semiconductor wafer according to the third embodiment will be described with reference to the drawings. FIG. 7 is a plan view showing the method of inspecting a semiconductor wafer according to the third embodiment of the present invention.

As shown in FIG. 7, in the method of inspecting a semiconductor wafer according to this embodiment, before a concentrated HF treatment and an SPM treatment for removing a semiconductor device structure (step S1), a third protected area, which is a part of the surface of the semiconductor wafer that is intended for crystal defect measurement based on photographic observation using the SEM, TEM or the like, is coated with a mask material (step S13).

Taking into account the following concentrated HF treatment and SPM treatment or the like, a tetrafluoroethylene tape, which has a relatively high resistance to etching, is selected as the mask material for coating the third protected area.

After step S13, as in the first embodiment, the concentrated HF treatment and the SPM treatment (step S1) and a diluted HF treatment and a rinsing and drying treatment (step S2) are carried out to completely remove the device structure film on the semiconductor wafer, thereby exposing the crystal surface of the semiconductor wafer.

Then, a fourth protected area, which is a part of the surface of the semiconductor wafer other than the third protected area, is coated with a mask material (Step S14). Here, FIG. 8 is a plan view of an exemplary semiconductor wafer coated with a mask material in the method of inspecting a semiconductor wafer according to the third embodiment of the present invention.

Figure 8:
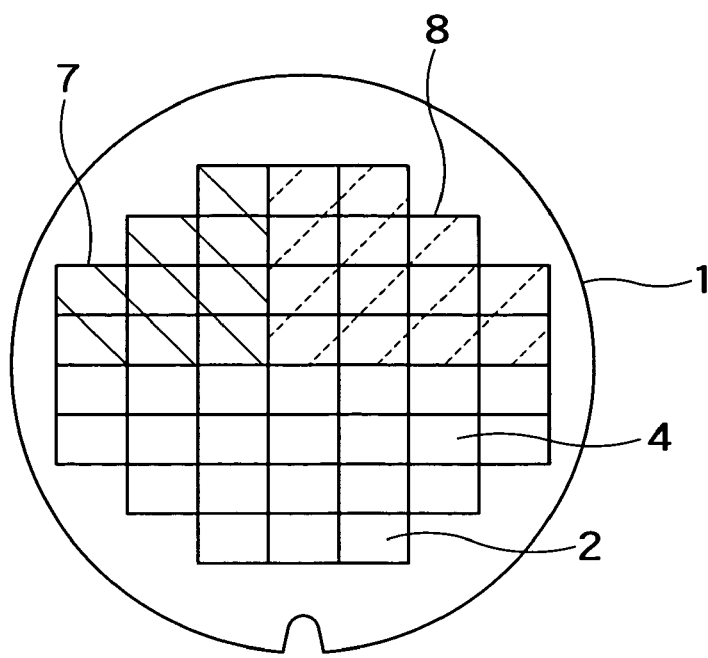
FIG. 8 is a plan view of a semiconductor wafer coated with a mask material according to the method of inspecting a semiconductor wafer according to the third embodiment of the present invention.

As shown in FIG. 8, nine chips are designated as a third protected area 7, and the third protected area 7 is coated with a tetrafluoroethylene tape as a mask material. Besides, thirteen chips adjacent to the third protected area 7 are designated as a fourth protected area 8, and the fourth protected area 8 is coated with a polyimide tape as a mask material. Thus, the remaining twenty-two chips, which are a half of the chips in the semiconductor wafer, are designated as a non-protected area 4.

Then, as in the first embodiment, the semiconductor wafer is selectively etched (step S4), the mask material is removed (step S5), and cleaning is performed (step S6). After that, the fourth protected area and the non-protected area, which is not protected by any mask material, are quantitatively measured by an optical defect inspection apparatus or a beam-type defect inspection apparatus. Furthermore, a chip in the third protected area of the semiconductor wafer is cleaved to directly measure the crystal defects of the chip, on which the device structure can remain, by photographic observation by the TEM. In addition, a chip in the non-protected area is cleaved to measure the etch pits (crystal defects) that have appear because of the selective etching by photographic observation by the SEM (step S15).

Then, based on the measurement result, the number of crystal defects of the semiconductor wafer is calculated (step S16). As in the first embodiment, the number of relevant crystal defects of the semiconductor wafer that are generated because of the manufacture process or the like can be determined by calculating the difference between the quantitative measured value for the fourth protected area and the quantitative measured value for the non-protected area. In addition, from the result of measurement by the TEM and the SEM, the number of crystal defects of the semiconductor wafer is determined, which allows verification of the reliability of the number of crystal defects determined by the quantitative measurement. In this way, the TEM measurement and the SEM measurement can be carried out using the wafer for the quantitative measurement without the need of preparing an additional sample wafer. Furthermore, since the measurements are carried out for the same wafer, the effect of lot-to-lot or wafer-to-wafer variations on the crystal defect measurement can be reduced, for example.

Here, crystal defects of a semiconductor wafer having a semiconductor device structure film formed thereon were measured using an optical defect inspection apparatus, an SEM and a TEM according to the flow shown in FIG. 7, and the measured values were compared. Now, the result of the comparison will be described.

First, one 8-inch semiconductor wafer having semiconductor device structure film formed thereon as described below was prepared as an evaluation sample and treated according to the method of inspecting a semiconductor wafer according to this embodiment to measure the crystal defects thereof.

Figure 9:
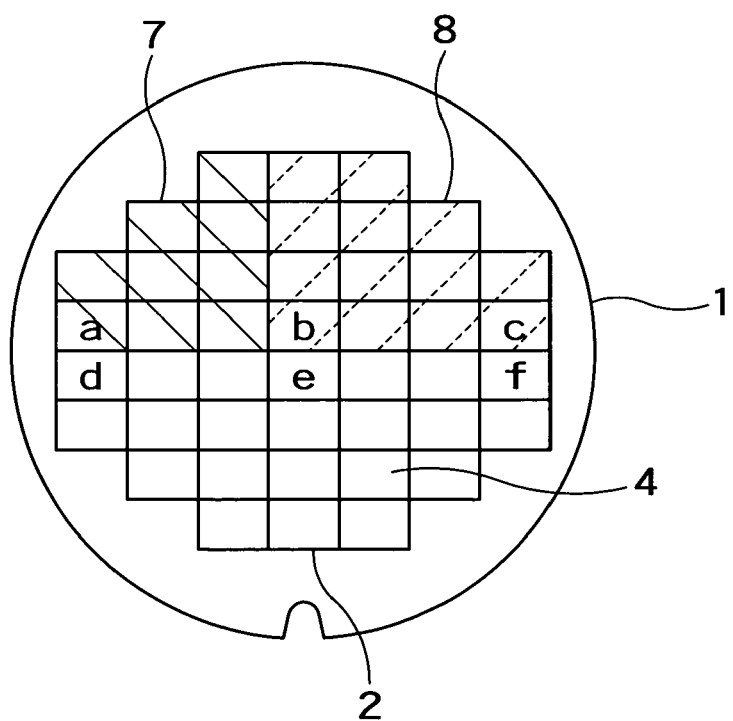
FIG. 9 is a plan view of a semiconductor wafer coated with a mask material according to the method of inspecting a semiconductor wafer according to the third embodiment of the present invention.

In the wafer, nine chips were designated as a protected area 7 as shown in FIG. 9, and a tetrafluoroethylene tape as a mask material was applied to the protected area 7 to cover the chips. In addition, thirteen chips adjacent to the third protected area 7 were designated as a fourth protected area 8, and a polyimide tape was applied to the fourth protected area 8 to cover the chips.

For measurement, a chip "a" in the third protected area 7 located at the left end of the wafer, a chip "d" in the non-protected area 4 that is adjacent to the chip "a", a chip "b" in the fourth protected area 8 located at the center of the wafer, a chip "e" in the non-protected area 4 that is adjacent to the chip "b", a chip "c" in the fourth protected area 8 located at the right end of the wafer, and a chip "f" in the non-protected area 4 that is adjacent to the chip "c" were selected.

As for the chip "a", on which the device structure remains, a thin Si sample piece that is parallel to the surface of the chip "a" was prepared, a picture of the sample piece was taken by plane TEM observation, and the number of crystal defects of the chip "a" was determined based on the picture. As for the chips "b" to "f", quantitative measurement based on image recognition by the optical defect inspection apparatus was carried out. In addition, as for the chip "d", which was subjected to the selective etching, SEM photographic observation was also carried out.

The result of measurement under the conditions described above is shown in FIG. 10. First, the number of crystal defects (crystal defect densities) of the chips determined by calculation based on the quantitative measurement by the optical defect inspection apparatus fell within a range of 5400 to 6200 defects/cm$^2$, as shown in FIG. 10.

As for the chips "e" and "f", the number of crystal defects was calculated using the quantitative measured values of their respective adjacent chips "b" and "c" as a noise component. For example, the quantitative measured value for the non-protected area (chip "e") was 26900 defects/cm$^2$, and the quantitative measured value for the protected area (chip "b") was 21500 defects/cm$^2$. Thus, the number of crystal defects, which is determined by the difference between the quantitative measured value for the non-protected area and the quantitative measured value for the protected area, was 5400 defects/cm$^2$. In this way, by comparing quantitative measured values between adjacent areas (chips), the effect of in-plane variations of the wafer on the number of crystal defects can be reduced.

The quantitative measurement by the defect inspection apparatus was not performed for the chip "a", because the chip "a" was not subjected to the complete removal. Therefore, the average value (21000 defects/cm$^2$) of the quantitative measured values for the chips "b" and "c" was compared with the quantitative measured value for the chip "d" to cancel the noise component in the quantitative measured value for the chip "d".

In addition, the number of crystal defects determined by SEM photographic observation was 5900 defects/cm$^2$ (chip "d") as shown in FIG. 10. The number of crystal defects determined by TEM photographic observation was 6100 defects/cm$^2$ (chip "a") as shown in FIG. 10.

As can be seen from the above description, the numbers of crystal defects (crystal defect density) determined by the method according to the present invention substantially coincide with the numbers of crystal defects determined by SEM and TEM photographic observation of dislocations in chips cut from the wafer. In this way, for example, in order to verify the reliability of the measured value for a wafer sample determined by the defect inspection apparatus based on the image recognition, the crystal defects of the same wafer sample can be measured by TEM and SEM photographic observation.

As described above, according to the method of inspecting a semiconductor wafer according to this embodiment, as in the first embodiment, the number of crystal defects of the semiconductor wafer generated due to a relevant manufacture process can be determined, and crystal defects of one wafer can be measured by various kinds of methods (TEM and SEM photographic observation), so that an optimal measurement method can be selectively used, and the reliability of the measured value can be improved. In addition, the number of sample wafers used for the inspection can be significantly reduced.

What is claimed is:

1. A method of inspecting a semiconductor wafer, comprising:
    removing a device structure film on the semiconductor wafer with a chemical solution to expose a crystal surface of the semiconductor wafer;
    coating a protected area, which is a part of the crystal surface of the semiconductor wafer, with a mask material for protecting the crystal surface of the semiconductor wafer;
    etching the semiconductor wafer selectively, thereby making a crystal defect in a non-protected area, which is a part of the crystal surface of the semiconductor wafer that is not coated with the mask material, appear after the crystal surface is coated with the mask material;

removing the mask material after the selective etching;

carrying out quantitative measurement of the protected area and the non-protected area using an optical defect inspection apparatus or a beam-type defect inspection apparatus; and calculating a number of crystal defects of the semiconductor wafer base on the result of the measurement.

2. The method of inspecting a semiconductor wafer according to claim 1, wherein the number of crystal defects of the semiconductor wafer is calculated based on the difference between the measured value for the protected area and the measured value for the non-protected area.

3. The method of inspecting a semiconductor wafer according to claim 1, wherein a plurality of protected areas of the crystal surface of the semiconductor wafer are coated with the mask material.

4. The method of inspecting a semiconductor wafer according to claim 1, wherein the quantitative measurement is carried out for a non-protected area adjacent to the protected area.

5. The method of inspecting a semiconductor wafer according to claim 1, wherein, in case where the device structure film on the semiconductor wafer is removed in a plurality of processes, coating a first protected area, which is a part of the surface of the semiconductor wafer, with a mask material during an interval between the plurality of processes;

coating a second protected area, which is a part of the surface of the semiconductor wafer other than the first protected area, with a mask material after the device structure film on the semiconductor wafer is removed to expose the crystal surface of the semiconductor wafer;

etching the semiconductor wafer selectively to remove the mask materials and then carrying out quantitative measurement of the first protected area, the second protected area and the non-protected area using the optical defect inspection apparatus or the beam-type defect inspection apparatus; and calculating the number of crystal defects of the semiconductor wafer based on the result of the measurement.

6. The method of inspecting a semiconductor wafer according to claim 5, wherein the number of crystal defects of the semiconductor wafer is calculated based on the difference between the measured value for the second protected area and the measured value for the non-protected area, and information for controlling the processes of removing the device structure film is obtained by calculating the difference between the measured value for the first protected area and the measured value for the second protected area.

7. The method of inspecting a semiconductor wafer according to claim 5, wherein the quantitative measurement is carried out for a non-protected area adjacent to the protected area.

8. The method of inspecting a semiconductor wafer according to claim 1, comprising:

coating a third protected area, which is a part of the surface of the semiconductor wafer, with a mask material before removing the device structure film on the semiconductor wafer;

coating a fourth protected area, which is a part of the surface of the semiconductor wafer other than the third protected area, with a mask material after the device structure film on the semiconductor wafer is removed to expose the crystal surface of the semiconductor wafer;

etching the semiconductor wafer selectively to remove the mask materials, carrying out quantitative measurement of the fourth protected area and the non-protected area using the optical defect inspection apparatus or the beam-type defect inspection apparatus, and carrying out measurement of the third protected area by photographic observation using a transmission electron microscope; and calculating the number of crystal defects of the semiconductor wafer based on the result of the measurements.

9. The method of inspecting a semiconductor wafer according to claim 8, wherein the quantitative measurement is carried out for a non-protected area adjacent to the protected area.

10. The method of inspecting a semiconductor wafer according to claim 1, wherein the mask material is a tetrafluoroethylene tape.

11. The method of inspecting a semiconductor wafer according to claim 10, wherein any of a diluted hydrogen fluoride treatment, a concentrated hydrogen fluoride and an SPM treatment is carried out in addition to the selective etching.

12. The method of inspecting a semiconductor wafer according to claim 1, wherein the mask material is a resist.

13. The method of inspecting a semiconductor wafer according to claim 1, wherein the mask material is a polyimide tape.

14. The method of inspecting a semiconductor wafer according to claim 1, wherein the mask material is a wax.

* * * * *